(12) United States Patent
Milbocker

(10) Patent No.: US 7,044,982 B2
(45) Date of Patent: May 16, 2006

(54) SURGICAL REPAIR OF TISSUE DEFECTS

(76) Inventor: Michael Milbocker, 1110 Washington St., Holliston, MA (US) 01746

( * ) Notice: Subject to any disclaimer, the term of this patent is extended or adjusted under 35 U.S.C. 154(b) by 21 days.

(21) Appl. No.: 09/939,863

(22) Filed: Aug. 27, 2001

(65) Prior Publication Data

US 2002/0049503 A1    Apr. 25, 2002

Related U.S. Application Data

(63) Continuation-in-part of application No. 09/692,963, filed on Oct. 20, 2000, now Pat. No. 6,296,607.

(51) Int. Cl.
*A61F 2/02* (2006.01)

(52) U.S. Cl. .................. 623/23.72; 606/151; 606/214

(58) Field of Classification Search ............ 623/23.72, 623/23.41; 128/898; 606/214, 215, 151–158
See application file for complete search history.

(56) References Cited

U.S. PATENT DOCUMENTS

| | | | |
|---|---|---|---|
| 3,054,406 A | 9/1962 | Usher | |
| 3,124,136 A | 3/1964 | Usher | |
| 3,272,204 A | 9/1966 | Atrandi et al. | |
| 3,376,869 A | 4/1968 | Borysko | |
| 3,563,228 A | 2/1971 | Seiderman | |
| 4,049,592 A | 9/1977 | Marans et al. | |
| 4,140,126 A | 2/1979 | Choudhury | |
| 4,193,137 A | 3/1980 | Heck | |
| 4,347,847 A | 9/1982 | Usher | |
| 4,403,604 A | 9/1983 | Wilkinson et al. | |
| 4,441,215 A | 4/1984 | Kaster | |
| 4,452,245 A | 6/1984 | Usher | |
| 4,520,821 A | 6/1985 | Schmidt et al. | |
| 4,577,631 A * | 3/1986 | Kreamer | 606/108 |
| 4,652,264 A | 3/1987 | Dumican | |
| 4,655,221 A | 4/1987 | Devereux | |
| 4,693,720 A | 9/1987 | Scharnberg et al. | |
| 4,710,192 A | 12/1987 | Liotta et al. | |
| 4,728,328 A | 3/1988 | Hughes et al. | |
| 4,769,038 A | 9/1988 | Bendavid et al. | |
| 4,781,191 A | 11/1988 | Thompson | |
| 4,804,691 A * | 2/1989 | English et al. | 523/118 |
| 4,838,884 A | 6/1989 | Dumican et al. | |
| 4,841,948 A | 6/1989 | Bauer et al. | |
| 5,002,551 A | 3/1991 | Linsky et al. | |
| 5,116,357 A | 5/1992 | Eberbach | |
| 5,122,155 A | 6/1992 | Eberbach | |
| 5,141,515 A | 8/1992 | Eberbach | |
| 5,146,933 A | 9/1992 | Boyd | |
| 5,147,374 A | 9/1992 | Fernandez | |
| 5,156,613 A * | 10/1992 | Sawyer | 606/213 |
| 5,209,776 A | 5/1993 | Bass et al. | |

(Continued)

FOREIGN PATENT DOCUMENTS

WO    WO 96/03925    2/1996

(Continued)

*Primary Examiner*—Paul B. Prebilic
(74) *Attorney, Agent, or Firm*—Francis H. Kirkpatric

(57) ABSTRACT

A method for repairing a defect in living mammalian tissue comprising: covering a tissue defect and surrounding tissue with a prosthetic by placing the prosthetic over the defect and against the surrounding tissue. The method includes applying a surgical adhesive to the prosthetic on the surrounding tissue on at least one location on the prosthetic and the surrounding tissue so that surrounding tissue and the prosthetic adhere to each other.

11 Claims, 7 Drawing Sheets

U.S. PATENT DOCUMENTS

| | | | |
|---|---|---|---|
| 5,258,000 A | 11/1993 | Gianturco | |
| 5,292,328 A | 3/1994 | Hain et al. | |
| 5,356,432 A | 10/1994 | Rutkow et al. | |
| 5,383,477 A | 1/1995 | DeMatteis | |
| 5,445,597 A * | 8/1995 | Clark et al. | 602/48 |
| 5,487,897 A * | 1/1996 | Polson et al. | 424/426 |
| 5,569,273 A | 10/1996 | Titone et al. | |
| 5,593,441 A | 1/1997 | Lichtenstein | |
| 5,634,931 A | 6/1997 | Kugel | |
| 5,665,106 A * | 9/1997 | Hammerslag | 606/214 |
| 5,695,525 A | 12/1997 | Mulhauser et al. | |
| 5,716,408 A | 2/1998 | Eldridge et al. | |
| 5,716,409 A | 2/1998 | Debbas | |
| 5,725,577 A | 3/1998 | Saxon | |
| 5,733,337 A | 3/1998 | Carr, Jr. et al. | |
| 5,743,917 A | 4/1998 | Saxon | |
| 5,755,658 A | 5/1998 | Wallace et al. | |
| 5,766,246 A | 6/1998 | Mulhauser et al. | |
| 5,769,864 A | 6/1998 | Kugel | |
| 5,785,642 A | 7/1998 | Wallace et al. | |
| 5,813,975 A | 9/1998 | Valenti | |
| 5,824,015 A | 10/1998 | Sawyer | |
| 5,904,648 A | 5/1999 | Arndt et al. | |
| 5,916,225 A | 6/1999 | Kugel | |
| 5,954,767 A | 9/1999 | Pajotin et al. | |
| 5,968,090 A | 10/1999 | Ratcliff et al. | |
| 5,972,007 A | 10/1999 | Sheffield et al. | |
| 6,004,333 A | 12/1999 | Sheffield et al. | |
| 6,004,341 A | 12/1999 | Zhu et al. | |
| 6,022,359 A | 2/2000 | Frantzen | |
| 6,022,372 A | 2/2000 | Kontos | |
| 6,191,216 B1 * | 2/2001 | Ganster et al. | 524/779 |
| 6,211,335 B1 * | 4/2001 | Owen et al. | 530/350 |
| 6,296,607 B1 | 10/2001 | Milbocker | |
| 6,312,442 B1 | 11/2001 | Kieturakis et al. | |
| 6,398,797 B1 * | 6/2002 | Bombard et al. | 606/153 |
| 6,485,513 B1 * | 11/2002 | Fan | 623/1.36 |
| 6,524,327 B1 | 2/2003 | Spacek | |
| 6,589,269 B1 * | 7/2003 | Zhu et al. | 606/214 |
| 6,592,515 B1 * | 7/2003 | Thierfelder et al. | 600/37 |
| 6,610,006 B1 * | 8/2003 | Amid et al. | 600/37 |
| 6,702,731 B1 | 3/2004 | Milbocker | |
| 6,793,676 B1 * | 9/2004 | Plouhar et al. | 623/14.12 |
| 2002/0028980 A1 * | 3/2002 | Thierfelder et al. | 600/37 |
| 2002/0049363 A1 | 4/2002 | Milbocker | |
| 2002/0173807 A1 * | 11/2002 | Jacobs | 606/151 |
| 2003/0135238 A1 | 7/2003 | Milbocker | |
| 2003/0188755 A1 | 10/2003 | Milbocker | |
| 2003/0194505 A1 | 10/2003 | Milbocker | |
| 2004/0068078 A1 | 4/2004 | Milbocker | |

FOREIGN PATENT DOCUMENTS

| | | |
|---|---|---|
| WO | WO 96/07355 | 3/1996 |
| WO | WO 96/09795 | 4/1996 |

* cited by examiner

SURGICAL REPAIR OF TISSUE DEFECTS

This application is a continuation-in-part of U.S. Ser. No. 09/692,963, now U.S. Pat. No. 6,296,607, entitled "In-Situ Bulking Device", filed Oct. 20, 2000, which is incorporated herein by reference in its entirety.

BACKGROUND OF THE INVENTION

1. Field of the Invention

Field of the Invention. This invention relates to surgical devices and procedures, and more particularly for the repair and augmentation of mammalian tissue utilizing a combination of adhesives and prosthetics, such repair, for example treating an inguinal hernia.

2. Prior Art

The surgical repair treatment of inguinal hernias fall into two groups: repairs that involve suturing the prosthesis to the surrounding muscular aponeurotic structures, such as Lichtenstein's operation; and the repairs that involve application of a sutureless prosthesis such as Gilbert's operation.

In the current medical practice, the established procedure in the surgical field is to use mesh, absorbable and non-absorbable, to repair defects in tissue. In inguinal hernia repair Prolene™ mesh and Mersilene™ (manufactured and sold by Ethicon, Inc., Somerville, N.J.) is sometimes used. Marlex™ mesh, an Atlas polypropylene monofilament knit, has also been used. Polypropylene is used because it promotes a fibroblastic response, but this response is only important for ensuring mesh fixation, it is also considered to be too stiff. Knitted and woven fabrics constructed from a variety of synthetic fibers have been used in surgical repair, among other, U.S. Pat. Nos. 3,054,406; 3,124,136; 4,193,137; 4,347,847; 4,452,245; 4,520,821; 4,633,873; 4,652,264; 4,655,221; 4,838,884; 5,002,551; and, European Patent Application No. 334,046.

In mesh applications, generally the mesh is cut to a desired size during the operation. Once the sized mesh has been placed over the defect, the mesh is attached to the surrounding tissue using several known attachment means. The need to shape the mesh during the surgery increases the duration of the surgery and also makes optimal fitting difficult.

The purpose for placing the mesh is: 1) to serve as a barrier over the defect in order to restrict the lower viscera in the patient's abdomen from protruding through the defect. To successfully fulfill the purpose the mesh must be attached with an initial strength of several pounds of force in both the tensile and shear directions. It is also essential that the mesh remain in place for several days so that natural adhesions can form to ensure that the mesh is sufficiently anchored to the tissue.

Commonly mesh is attached to tissue with sutures. Suturing requires a great deal of skill, especially for minimally invasive or laparoscopic procedures. The difficulty in placing sutures is a primary barrier to the general adoption of laparoscopic procedures.

Surgical staplers have been introduced as an alternative to sutures. A surgical stapler such as ENDOSCOPIC MULTI-FIRE STAPLER™, (manufactured and sold by Ethicon Endo-Surgery, Inc., Cincinnati, Ohio) has been used. U.S. Pat. No. 5,470,010 (Rothfuss et al.) discloses a disposable, endoscopic stapler that is used to place a number of staples at various locations of the placed mesh in order to properly secure the mesh.

Both the suture and staple approaches risk a variety of complications. Frequently, because of possible excessive tension and bad distribution of the prosthesis, it isn't able to dynamically suit the modification of relationships among the anatomic structures of the inguinal canal and because it is suture along its periphery. This produces pain that can be felt during movements of the muscular-aponeurotic structures in the inguinal region. The sutures themselves can cause vascular lesions, tissue lacerations, and nerve lesions.

In the prior art, there are also several "sutureless" techniques for inguinal hernia repair. The mesh is applied without suturing by including an underfascial plug placed in the internal inguinal orifice. Plugs however, have their own problems. Perception of an inguinal tumefaction connected to sclerosis stimulated by the presence of the plug is experienced as discomfort by the patient. Displacement of the plug can involve contact of the plug with the extraperitoneal organs and cause possible bedsores on the viscera. Relapses after using the plug are difficult to treat. There is difficulty in treating postoperative suppuaration (formation of pus) because the presence of the underfascial plug cannot be cleaned with superficial dressing. Given the hernia rate in the United States population, the constant use of properitoneal underfascial plugs could cause a significant amount of risk to patients because of possible prosthetic infection if an operation were necessary for a pelvic septic pathology such as tumor of the colon, appendicitis, or surgeries of the prostate and bladder. The plug also tends to displace on the operating table, forcing surgeons to secure the mesh with stitches, thus undermining the sutureless advantage.

Mesh displacement may occur when motion from a supine position to an upright position modifies the reciprocal relationships among the inguinal muscular aponeurotic structures, a sutureless mesh in the upper facial region which is connected to a plug can later displace from the implanted position. The possibility of raising the prosthesis is increased, mainly in the pubis region, which is encountered in the frequent relapses in this area. In the case of the unsutured prosthesis, the fibroplastic reaction is delayed and hindered by the mesh mobility. A cicatricial retraction can ensue acting to additionally deform the mesh. Finally, if the sutureless technique is used in the case of an external oblique inguinal hernia, the yielding of the transversalis layer is coupled with the yielding of the external inguinal ring and of the aponeurosis of the great oblique, said aponeurosis sometimes becomes a fibrous, sliding veil unsuitable to support the prosthesis under abdominal pressure.

U.S. Pat. No. 5,972,007 (Sheffield et al.) discloses an energy-base method applied to prosthetics for repairing tissue defects. The method risks tissue damage from the energy required to be deposited in the tissue to bond collagen pads to living tissue.

An alternative to the mesh is the use of a conical mesh plug which is sometimes placed without attachment. The technique is used in closing abdominal defects, sometimes simply by folding a surgical mesh into a multi-layer cone configuration. Preformed conical mesh plugs have been proposed. C. R. Bard makes a "Marlex Mesh Dart" also known as PerFix®. This implant is heat molded and stiff, and does not conform to irregularities in the muscle or tissue wall defining the defect.

U.S. Pat. No. 5,356,432 (Rutkow et al.) describes an implantable prosthesis including a conical mesh plug having a pleated surface which conforms to the contours of the defect being repaired. Mesh filler is applied to stiffen the implant. However, there is provided no means for fixing the implant position.

With respect to endoscopic techniques, concerns have been raised about visualization light reflected from the fabric surface during laparoscopy, impairing visualization of the prosthetic material and underlying anatomy. Increasing the pore size of the mesh helps, but also diminishes the physical properties of the implant necessary for augmentation or repairing abdominal tissue.

It is an object of the present invention to provide a prosthetic and method for repairing a defect in tissue that is minimally invasive, time and cost effective and easy to use.

It is another object of the present invention to provide a method and prosthetic for facilitating the repair of tissue defects that does not involve sutures, clips, tacks, or staples for stabilization of the prosthetic.

It is another object of the present invention to provide a prosthetic for tissue repair which is characterized by a porosity that allows surgeons to see through the prosthetic during laporoscopy as well as classical open procedures.

It is another object of the invention to provide a prosthetic for tissue repair with a color pattern which facilitates the orientation and/or installation of the mesh at the surgical repair site.

An object of the present invention is the provision of a two-part prosthetic, one side of which prevent or minimizes organ adhesion and surgical adhesive adhesion.

It is thus a primary object of the present invention to overcome the disadvantages of the prior art.

It is another object of the present invention to employ a plug geometry in combination with a surgical adhesive for the repair of hernias including: a plug positionable in an opening in the abdominal wall, a patch positionable over weakened portions of the abdominal part adjacent to the opening, a central extent of the patch being coupled to the proximal end of the plug, and a resilient means coupled to the patch and provided with memory to assume a configuration of an extended shape for the proper positioning of the patch with respect to the weakened portions of the abdominal part.

It is a yet a further object of the present invention to use surgical adhesive in conjunction with a plug to provide bulk to the plug after placement, to provide prosthetic stabilization, and to provide a close fit between plug and surrounding tissue.

It is an additional object of the present invention to provide a prosthetic that can be augmented by the use of a surgical adhesive for the repair of varying sizes and shapes of hernias.

It is yet a still further object of the present invention to disclose a prosthetic combination which lessens or eliminates tractions and tensions inherent to a prosthetic peripherally sutured.

It is another further object of the present invention to provide free and autonomous movement of two prosthetic components.

It is a further object of the present invention to minimize the time, cost and patient discomfort of hernia operations.

It is a further object of the present invention to reduce or preclude the recurrence of hernias.

It is a further object of the present invention to eliminate complication risks associated with the use of staples, sutures or other tissue disruptive means for stabilizing the prosthetic.

BRIEF SUMMARY OF THE INVENTION

The present invention is directed toward surgical procedures where reinforcement or repair of tissue by such surgery provides a functional or aesthetic result. Such an invention comprises both a novel device and method for use in repairing a mammalian tissue. The method and prosthetic according to the present invention essentially combines the use of a surgical adhesive with a reinforcing fabric which is useful for various types of surgical procedures, and is particularly useful for the repair of an inguinal hernia.

Methods comprising the present invention particularly for repairing a defect in a mammalian tissue, such as an inguinal hernia, include placing of a prosthetic over a tissue defect and also against the tissue surrounding the defect. A surgical adhesive is applied to the prosthetic to at least one location on the prosthetic and also on the surrounding tissue until surrounding tissue and the prosthetic adhere to each other.

A prosthetic according to the present invention may take several preferred embodiments. The prosthetic may in a first embodiment, include use of a readily available mesh structure already in use, such as polypropylene mesh. It may also as a further embodiment, include the use of PTFE in the form of a mesh or as a non-porous non-adherent layer. It may also, in yet a further embodiment, be constructed of various absorbable sheets such as preserved bovine pericardium.

The present invention provides a prosthetic and a method for repairing a defect in tissue that is minimally invasive, time and cost effective and easy to use, and provides a method and prosthetic for facilitating the repair of tissue defects that does not involve sutures, clips, tacks, or staples for stabilization of the prosthetic, while providing a prosthetic for tissue repair which is characterized by a porosity that allows surgeons to see through the prosthetic during laporoscopy as well as classical open procedures. It provides a prosthetic for tissue repair with a color pattern which facilitates the orientation and/or installation of the mesh at the surgical repair site. It includes a provision of a two-part prosthetic, one side of which prevent or minimizes organ adhesion and surgical adhesive adhesion. It employs a plug geometry in combination with a surgical adhesive for the repair of hernias including: a plug positionable in an opening in the abdominal wall, a patch positionable over weakened portions of the abdominal part adjacent to the opening, a central extent of the patch being coupled to the proximal end of the plug, and a resilient means coupled to the patch and provided with memory to assume a configuration of an extended shape for the proper positioning of the patch with respect to the weakened portions of the abdominal part. A surgical adhesive may be used in conjunction with a plug to provide bulk to the plug after placement, to provide prosthetic stabilization, and to provide a close fit between plug and surrounding tissue. The prosthetic may be augmented by the use of a surgical adhesive for the repair of varying sizes and shapes of hernias. The prosthetic combination may lessen or eliminate tractions and tensions inherent to a prosthetic peripherally sutured. The present invention provides free and autonomous movement of two prosthetic components, minimizes the time and cost of hernia operations, and minimizes a patient's discomfort associated with a hernia operation. The prosthetic for tissue repair may include a color pattern which facilitates the orientation and/or installation of the mesh at the surgical repair site. A two-part prosthetic may have one side of which prevents or minimizes organ adhesion and surgical adhesive adhesion. A plug geometry is used in combination with a surgical adhesive for the repair of hernias including: a plug positionable in an opening in the abdominal wall, a patch positionable over weakened portions of the abdominal part adjacent to the opening, a central extent of the patch being coupled to the proximal end of the plug, and a resilient means coupled to the patch and provided with memory to assume a configuration of an extended shape for the proper positioning of the patch with respect to the weakened portions of the abdominal part. Surgical adhesive may be used in conjunction with a plug to provide bulk to the plug after placement, to provide prosthetic stabilization, to provide a close fit between plug and surrounding tissue, to provide a prosthetic that can be augmented by the use of a surgical adhesive for the repair of varying sizes and shapes of hernias, and to provide free and autonomous movement of two prosthetic components.

The prosthetic of this invention finds application in a number of surgical procedures including the repair of hernias, anatomical defects of the abdominal wall, diaphragm, and chest wall, correction of defects in the genitourinary system, repair of traumatically damaged organs such as the spleen, liver or kidney, etc.

The invention thus comprises a mesh intended to be implanted laparoscopically and constructed so as to allow for it to be delivered through a small hole or access port in the skin. Meshes delivered in this way are rolled into a cylinder, passed through a trocar in the access port and unfurled over the tissue defect. Additional instrumentation may be introduced in the access port for the purpose of suturing or stapling the mesh to the tissue. One of the complications of introducing an adhesive coated mesh in this way is the likelihood that it will adhere to itself or to surrounding tissue; and there is an additional need to be able to move the mesh around at the repair site before fixing.

To achieve this, a mesh may be coated with an adhesive and the resulting composition can be further coated with a water soluble coating or placed in a water soluble envelope. Methods for achieving this end include making sheets of ethyl or methyl cellulose, forming the sheets into pockets and slipping the adhesive coated mesh into the formed pocket. The pocket can then be sealed using heat or a nonaqueous solution of the sheet composition. In these constructions, the thickness of the coating and the type of coating determine solubility and hence time to release of adhesive at the implant site. This composition allows the mesh to be rolled into a cylinder, introduced into the body and unfurled without activation of the adhesive by contact with body fluids. Body fluids or additional water introduced into the site would then act on the coating to release the adhesive at a predetermined time. For example, the coating may be formed of suitable thickness to prevent contact of adhesive with tissue for several minutes. In this example, the coating would be methyl cellulose of about 200–800 micron thickness. Other coatings suitable for novel coating of the mesh are those utilized for coating orally administered pharmaceuticals.

In an alternative preferred embodiment, an adhesive coated mesh may be frozen using liquid nitrogen or other suitable coolant to render the adhesive a solid. A solution of the coating material may be prepared using a nonaqueous solvent. In the example of methyl cellulose, the solvent would preferably be chloroform or even acetic acid. The frozen mesh would next be dipped into the chloroform/methyl cellulose solution and then removed. The solvent is then rapidly driven out of the coating solution by passage of dry air. This is a "dip casting" technique. Multiple dips may be required to build a layer of suitable thickness and absent of defects. In a further preferred embodiment, the glue itself may be encapsulated and applied to the mesh. The encapsulation of the glue can be achieved using a similar dipping or rolling technique.

A mesh coated in this way permits repair of a tissue defect without the use of sutures or other fixing devices. The mesh is introduced through a trocar and positioned using available surgical instruments. Once positioned, which may take several minutes of moving the mesh with respect to the defect, the coating can be allowed to dissolve in the presence of existing fluids at the repair site. Alternatively, additional sterile saline can be introduced into the field to rapidly dissolve the protective coating. Once a solution permeates the coating, the adhesive dissolves into the fluid and comes into contact with tissue and adheres the device. It is important to note that the coating material must be biocompatible because it or solutions of it will be incorporated in the adhesive as it cures to tissue.

Polypropylene mesh used for the repair of tissue defects are clear and are formed in an open-weave structure. The ratio of open area to solid area is usually greater than 1. These mesh are suitable for the present invention. Even more open and flexible mesh are suitable in the present invention since the strength provided by the solid portion of the mesh can be reduced due to the binding, reinforcing, and filling character of the adhesive. For example, a mesh composed of fibers that are free to move with respect to one another would generally aneuryze when attached by sutures, but such meshes when filled with adhesive do not aneuryze, because the fibers are fixed by the adhesive. In this case, a mesh may have a porosity of 90% open area, or greater. Additionally the mesh material may be more flexible or even elastic since surface area dimensions would also be fixed by an encasing adhesive.

In further embodiments, mesh structures may be shaped to conform to certain anatomical structures, such as the sperm cord. Therefore, it may be advantageous to "color code" an edge of the mesh to indicate mesh orientation with respect to the structure of interest. Additionally, coating the tissue contacting surface more thickly than the surface away from the defect minimizes the overall bulk of the device and also facilitates its rolling. In this instance, the tissue contacting side may be indicated by coloring that surface. Alternatively, in yet another preferred embodiment, the non tissue contacting side may be formed of a slowly absorbing material, since dissolution of this side during the procedure is not required to achieve fixation of the device. The dissolution of this side may take several days or weeks. Devices coated in this way may be color coded to indicate the tissue contacting side.

In a further embodiment, the non-tissue contacting side may be formed of a slowly absorbed or non-absorbable material such as methyl- or ethyl cellulose which is intended to prevent tissue adhesion. Surrounding tissue that adheres to the mesh prevents movement of the defect repair site and may cause pain. Such a tissue adhesion-prevention surface may be formed of hyaluronic acid or similar compositions, such as polyethylene glycol or the like.

Mesh plugs may be utilized in combination with a mesh. An adhesive may be used to combine a plug with a mesh. In this example, the distal end of the plug would contain an adhesive that may be released by water, or alternatively, removing a protective surface and then have the mesh applied thereon. Or alternatively, the plug may contain no adhesive and the fixing mesh with adhesive is applied over the plug and surrounding tissue to fix the mesh and plug with respect to the surrounding tissue. A plug/path combination may be suitably colored or marked to indicate orientation. The patch may be woven in a surface varying fashion to provide greater flexibility around the portioned intended to couple with the plug. Additionally, the adhesive may be applied to the mesh surface to provide varying amounts and thickness of adhesive to provide varying levels of mesh support with respect to the plug position.

With respect to mesh and plug configuration, the mesh may contain excess adhesive in the form of an interfacing "coated and formed protuberance" of adhesive shaped to engage the plug and fix the orientation of the mesh with respect to the plug. Such a structure may fill the conical structure of the plug, and when released, it will adhere to and strengthen the plug in the implanted configuration. Thus an implant geometry can be fixed by the introduction of a substantially three-dimensional supporting-volume of adhesive. The plug may be increased in volume by the introduction of an adhesive volume that solidifies after implantation.

The coating structure may be used to delinear a region of adhesive applied to the mesh surface. For instance, there are particular advantages in providing a discrete covering of adhesive over the mesh surface so that fixation points are correlated to other fixation points through the flexibility of the mesh. Exemplary patterns may be stripes, circles in a uniform pattern, circles of increasing diameter near the center, wavy lines, and the like commonly used in various other adhesive applications. Such geometries may be intended to result in traction reduction features common to sutured and stapled meshes. For instance, as the mesh become ingrown with tissue, certain sites pull against other fixed sites. A mesh with elastic contact points may be preferred in the softening of such traction. Additionally, the adhesive composition may be absorbable or weakening over time to provide for fixation points to de-adhere to the tissue surface as ingrowth replaces the need for mesh fixation. In general, meshes are fixed peripherally, and the distribution of fixation points across the surface of the mesh will likely lessen the incidence of extreme traction at isolated points.

Delayed release of fixation through use of a coated adhesive or a slowly curing adhesive provide time for the clinician to move mesh and plug structure to positions that provide defect repair without localized stress, and further to provide optimal orientation between the two structures, or between a single mesh and anatomical structures.

Accordingly, the time and cost of a hernia repair or like tissue repairs is reduced by eliminating the need for specialized, disposable fixing devices and the reduction of peri-operative and post-operative complications. Adhesions between mesh and surrounding tissue are the primary source of post-operative pain. Adhesives applied in any configuration will likely reduce adhesions by physically separating one tissue surface from the another through an adhesive coated surface.

The invention thus comprises a method for repairing a defect in living mammalian tissue comprising covering a tissue defect and surrounding tissue with a prosthetic by placing the prosthetic over the defect and against the surrounding tissue; and applying a surgical adhesive to the prosthetic on the surrounding tissue on at least one location on the prosthetic and the surrounding tissue so that surrounding tissue and the prosthetic adhere to each other; applying the adhesive onto the prosthetic at several locations on the prosthetic and onto the surrounding tissue; applying the adhesive onto the prosthetic in situ through an endoscope; wherein the adhesive comprises a cyanoacrylate-based adhesive; or wherein the adhesive comprises a fibrin-based adhesive; or wherein the adhesive comprises a polyurethane-based adhesive. The polyurethane-based adhesive may include a foaming agent added to produce an open cell geometry upon curing in situ to promote tissue ingrowth. The method may include applying a light crosslinked albumin soldier to the prosthetic. The prosthetic may be an absorbable collagen material. The prosthetic may be formed of a material selected from the group consisting of: polytetrafluorethylene or a fibrotic polypropylene stimulator material. The tissue defect may be an inguinal hernia. The method may include placing at least one absorbent pad on the tissue; delivering the adhesive onto the absorbent pad on the tissue; and suturing the adsorbent pad to the prosthetic. The invention includes aq method for repairing a defect in living tissue comprising, attaching a syringe to a catheter; delivering a surgical adhesive through the catheter from the syringe to the tissue defect, and covering the tissue defect and surrounding tissue with the surgical adhesive, the surgical adhesive being mixed with a plurality of filaments of a second solid substance so that when the adhesive cures to the tissue the second solid provides a randomized matrix fully encapsulated by the adhesive. The filaments of the second solid may selected from the group comprised of polypropylene or e-PTFE measuring between 100 and 500 microns in length and between 25 and 100 microns in diameter, the filaments being mixed with the adhesive prior to application in a filament to adhesive volume ratio of about 1:10 to 1:2. The method may include mixing a portion of collagen spheres measuring between 100 and 500 microns in diameter with the adhesive prior to application onto the tissue, the spheres to adhesive mixed in a ratio of about 1:10 to 1:2. The prosthetic may comprise a mesh patch having at least one absorbent pad for delivering the adhesive and for forming a bond between the absorbent pad bearing the adhesive and the tissue.

The invention may include an implantable prosthesis for repairing a tissue or defect in a muscle wall comprising a flexible porous plug arranged to retain a surgical adhesive for creating a tissue bond, the plug arranged to fit within and occlude a tissue or muscle wall defect wherein at least a portion of the flexible plug includes a cavity which permits delivery of an additional adhesive into the plug so that the plug conforms to any irregularities in the tissue or muscle wall defining the defect to form a cured solid plug of adhesive and a flexible plug, the flexible plug being compressible radially upon insertion into the defect from a first configuration which is larger than the defect to a second configuration which closely approximates the shape of the defect. The flexible plug may be comprised of a cone of foamed and cured surgical adhesive within which an uncured adhesive is disposed. The plug may include a closed rounded first end, and an open second end and a cavity extending therebetween, the cavity arranged to receive a volume of surgical adhesive which stiffens the implantable prosthesis when the plug is compressed into the configuration and bonds to the surrounding tissue. The flexible plug may include a plurality of mesh petals.

The invention may also include a tissue defect repair patch for implanting within a patient, comprising at least one first layer of inert synthetic mesh material sized and shaped to extend across and beyond a tissue aperture in a patient; a resilient support member adjacent a periphery of the first layer for creating tension in the first layer, the support member being carried by the first layer so as to remain implanted with the first layer in the patient; the first layer of inert synthetic mesh material having a periphery extending beyond the support member to define a border which has a free outer edge to fill uneven voids in a patient's tissue. The first layer of inert synthetic mesh material having a surgical adhesive impregnated between interstices of the first layer to effect a bond between mesh and tissue. The invention includes a tissue defect repair patch for implanting within a patient, comprising: at least one layer of flexible, inert synthetic non-porous sheet sized and shaped to extend across and beyond a tissue aperture in a patient; a resilient support member adjacent a periphery of the layer for creating tension in the layer, the support member being carried by the layer so as to remain implanted with the layer in the patient; and the layer of inert synthetic sheet having a periphery extending beyond the support member, defining a border which has a free outer edge to fill uneven voids in a patient's tissue; and the layer of inert synthetic sheet having a surgical adhesive coating the sheet to effect a bond between mesh and tissue. The sheet may be comprised of a first substance encapsulating a surgical adhesive, such that when pressure is applied, the encapsulated surgical adhesive is ejected from the encapsulation sites to effect a bond between the ruptured cell structure and tissue. The patch may have a plurality of slits in the border. The invention may comprise a plug formed of non-porous material in which a central cavity allows for delivery of adhesive; and which further had a plurality of dart-shaped slits in the plug, creating dart-shaped tabs which protrude from said plug to engage tissue to retain the plug. The plug may be formed from a non-porous inflatable structure of conical geometry, in which surgical adhesive is injected to form the inflatable structure to fill a defect. The inflatable structure permits permeation of fluids into its interior, thus effecting a cure of the surgical adhesive. The plug may be formed from a porous inflatable structure of conical geometry, in which surgical adhesive is injected to form the inflatable structure to fill a defect. The porosity of the inflatable structure is such that adhesive slowly flows from the surface, such porosity being between 25–50 microns for a surgical adhesive with a viscosity of 3000 cps. The adhesive effects a bond between plug and tissue. The inflatable structure permits permeation of fluids into its interior, thus effecting a cure of the surgical adhesive. The porosity of the inflatable structure is matched to the viscosity of the surgical adhesive to effect a slow elusion of adhesive into contact with tissue. The adhesive may be increased or decreased in viscosity by an inert fluid therein. The invention also includes an implantable prosthesis for repairing a defect in a muscle or tissue wall, the prosthesis comprising: a sheet of surgical prosthetic material including an inner portion and a peripheral edge surrounding the inner portion, the inner portion having a preformed contoured shape curved in three dimensions that forms a cavity with an open end surrounded by the peripheral edge, the inner portion being constructed and arranged to conform to the wall and to minimize shifting of the prosthesis when adhesive is applied and the prosthesis is positioned on the wall, the peripheral edge including at least first and second opposed margins, the first margin having a first curvature and the second margin having a second curvature which is less than the first curvature.

BRIEF DESCRIPTION OF THE DRAWINGS

The objects and advantages of the present invention will become more apparent when viewed in conjunction with the following drawings in which.

DESCRIPTION OF THE PREFERRED EMBODIMENTS

Figure 1:
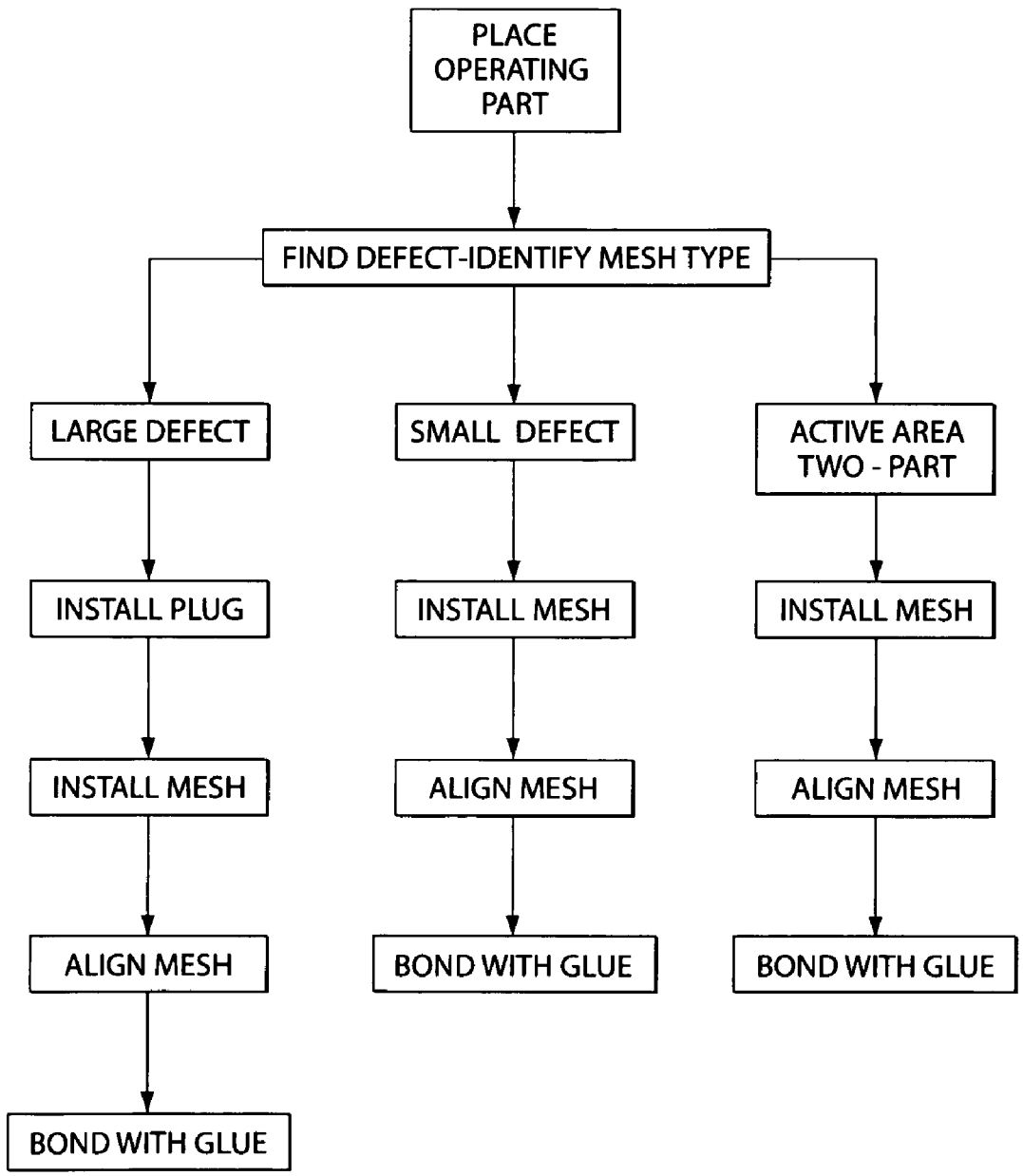
FIG. 1 is a block diagram of the steps in the surgical repair of tissue defects.
Figure 2A:
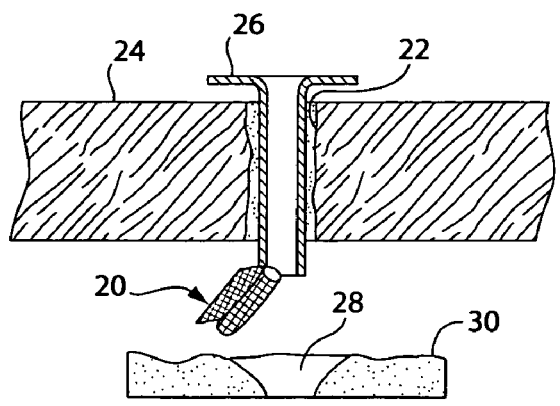
FIGS. 2a, 2b and 2c are sectional views of a procedure for tissue repair.
Figure 2B:
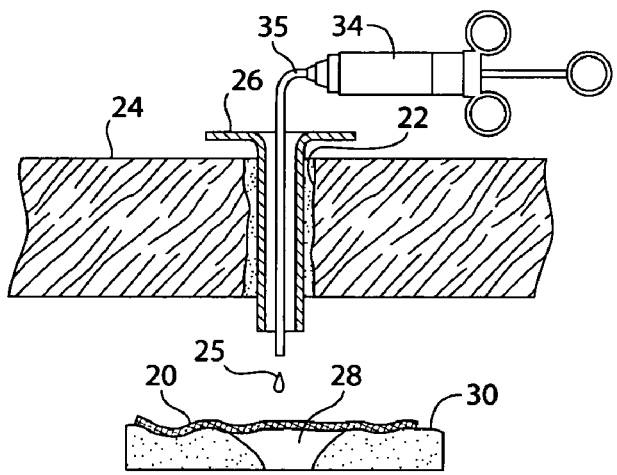
Figure 2C:
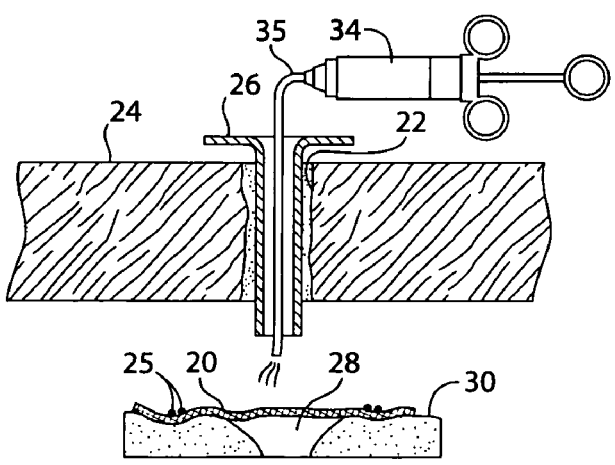

Referring now to the drawings in detail, and particularly to FIG. 1, there is shown in a block diagram format, the process of the present invention, and in FIGS. 2a, 2b and 2c, as schematic representations of the surgical repair apparatus and its associated procedure for treating tissue defects.

The invention thus comprises a mesh 20 intended to be implanted laparoscopically, as may be envisioned in FIGS. 2a–2c, and constructed so as to allow for it to be delivered through a small hole or access port 22 in the skin 24. Meshes 20 delivered in this way are preferably rolled into a cylinder, as shown in FIG. 2a, passed through a trocar 26 in the access port and unfurled over the tissue defect 28. Additional instrumentation may be introduced in the access port 22 for the purpose of suturing or stapling the mesh 20 to the tissue 30. One of the complications of introducing an adhesive coated mesh in this way is the likelihood that it will adhere to itself or to surrounding tissue, and there is an additional need to be able to move the mesh around at the repair site before fixing to the tissue.

Figure 3A:
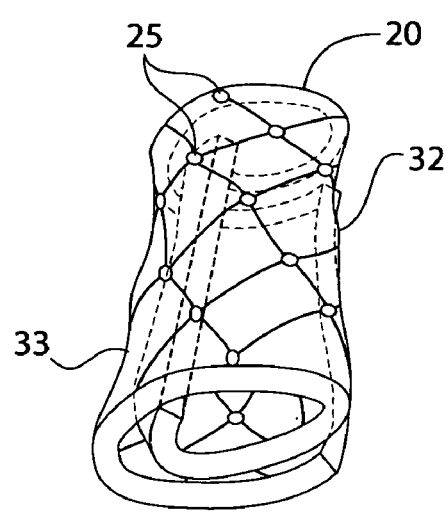
FIGS. 3a, 3b and 3c are representations of the mesh material utilized in the present procedure for tissue repair.
Figure 3B:
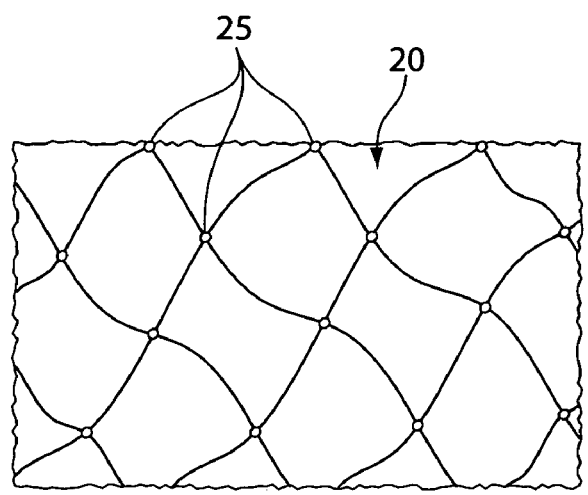
Figure 3C:
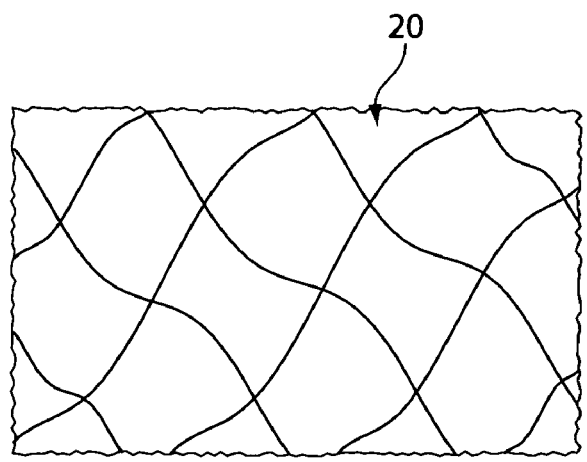

To achieve this, a mesh 20 may be coated with an adhesive 25 and the resulting composition can be further coated with a water soluble coating or placed in a water soluble envelope or sheet 32, as represented in FIG. 3a. Methods for achieving this end include making coatings or sheets 32 of ethyl or methyl cellulose, forming the sheets 32 into pockets 33 and slipping the adhesive coated mesh 20 into the formed pocket 33. The pocket 33 can then be sealed using heat or a non-aqueous solution of the sheet composition. In these constructions, the thickness of the coating and the type of coating determine solubility and hence time to release of adhesive 25 at the implant site. This composition allows the mesh 20 to be rolled into a cylinder, as shown in FIG. 3a, introduced into the body and unfurled without activation of the adhesive by contact with body fluids, as shown in FIG. 2a. Body fluids or additional water introduced into the site by a syringe or fluid injector 34, through a catheter 35 as shown in FIG. 2b, would then act on the coating to release the adhesive 25 at a predetermined time. For example, the coating 32 may be formed of suitable thickness to prevent contact of adhesive 25 with tissue 30 for several minutes. In this example, the coating 32 would be methyl cellulose of about 200–800 micron thickness. Other coatings suitable for novel coating of the mesh are those utilized for coating orally administered pharmaceuticals.

In an alternative preferred embodiment, an adhesive coated mesh 20 may be frozen using liquid nitrogen or other suitable coolant to render the adhesive a solid. A solution of the coating material may be prepared using a non-aqueous solvent. In the example of methyl cellulose, the solvent would preferably be chloroform or acetic acid. The frozen mesh may then be dipped into the chloroform/methyl cellulose solution and then removed. The solvent is then rapidly driven out of the coating solution by passage of dry air. This is a "dip casting" technique. Multiple dips may be required to build a layer of suitable thickness and absent of defects. In a further preferred embodiment, the adhesive or glue itself may be encapsulated and applied to the mesh 20. The encapsulation of the adhesive/glue can be achieved using a similar dipping or rolling technique.

A mesh coated in this way permits repair of a tissue defect without the use of sutures or other fixing devices. The mesh 20 may be thus introduced endoscopically, as through a trocar 26 and positioned using available surgical instruments. Once positioned, which may take several minutes of moving the mesh 20 with respect to the defect 28, the coating 32 can be allowed to dissolve in the presence of existing fluids at the repair site. Alternatively, additional sterile saline can be introduced into the field by the injector 34 and catheter 35 to rapidly dissolve the protective coating. Once a solution permeates the coating, the adhesive dissolves into the fluid and comes into contact with tissue 30 and adheres the mesh device 20. It is important to note that the coating material must be biocompatible because it or solutions of it will be incorporated in the adhesive as it cures to tissue.

Figure 4A:
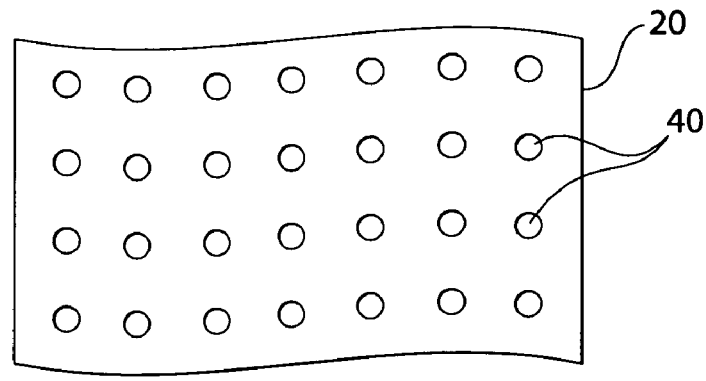
FIGS. 4a, 4b and 4c are representations of the mesh material utilized in the present invention with several embodiments therewith.
Figure 4B:
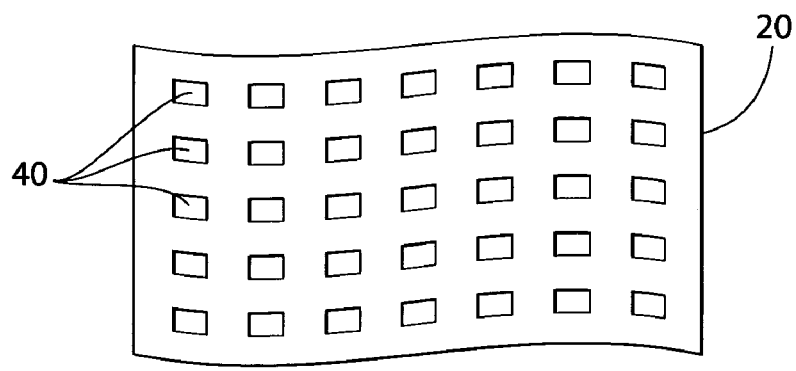
Figure 4C:
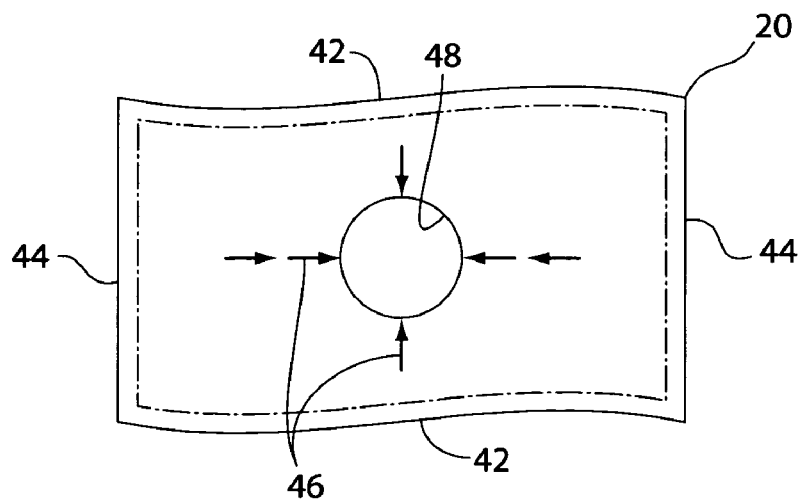

The mesh structure 20 itself, for attachment to living tissue may be made from, for example, polypropylene or a woven mesh. A polypropylene mesh may be made from a sheet of polypropylene with the openings 40 therein punched through such as shown in FIGS. 4a and 4b. The sheets of mesh 20 may have a pair of parallel long edges 42 and a pair of opposed parallel short edges 44, as shown in FIG. 4c. Each respective pair of parallel edges 42 and 44 may have a particular bright color to indicate which is the short edge 44 and which is the long edge 42. The mesh sheet 20 as also shown in FIG. 4c may have arrows 46 printed thereon indicating the direction/location of the hole 48 through that mesh sheet 20 where a plug would be deposited. Such an indication of directionality of the center hole 48 in the mesh sheet 20 is particularly useful in a situation of minimum accessability (i.e. laproscopic placement).

Figure 5A:
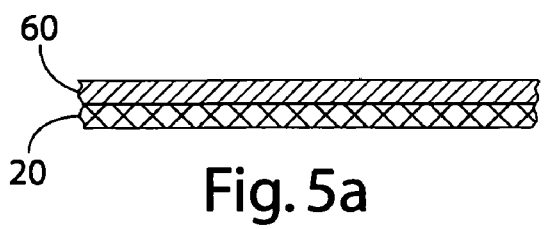
FIGS. 5a and 5b are sectional views of the mesh in combination with other layers of material utilized therewith.
Figure 5B:
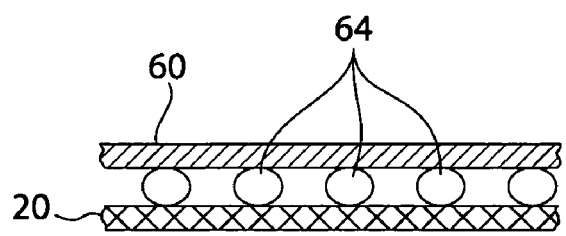

A further embodiment of the mesh sheet application as originally identified in the block diagram of FIG. 1, is depicted in a side elevational views in FIG. 5a and in FIG. 5b. A thin elastic barrier 60 such as PTFE, or silicone hydrogel may be applied to one side of the mesh sheet 20 prior to its application onto the tissue defect 28. The two part mesh sheet in yet a further embodiment, is shown in FIG. 5b wherein the thin protective layer 60 and the mesh sheet 20 sandwich an arrangement of encapsulated adhesive or glue capsules or globules 62 therebetween. The glue in the globules 62 is released by being squeezed between the protective layer 60 and the mesh sheet 20. The protective layer 60 directs the squeezed adhesive/glue within the globules 62 to the open surface side of the mesh sheet 20. Water may also be released by the disillusion of the glue in their capsules 62.

Figure 6A:
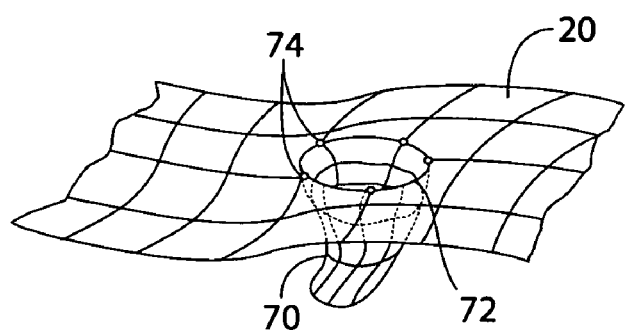
FIGS. 6a and 6b are perspective views of a combination of a mesh and a plug in various assemblies.

The basic mesh sheet 20 with a preferred central opening 48 therethrough is arranged to receive a plug 70 therein, as represented in FIG. 6a. The cylindrically shaped plug 70 may be bonded at its contacting end 72, with the mesh sheet 20 by an arrangement of adhesive or glue 74 disposed therearound. In a preferred procedure, the plug 70 is placed in the defect 28 in the tissue 30, then the mesh 20 is positioned with its opening on one end of that plug 70 and bonded thereto.

Figure 7A:
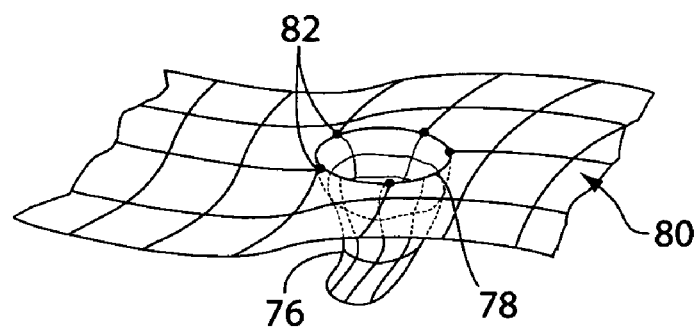
FIGS. 7a, 7b and 7c shown varying mesh formations with a plug.
Figure 7B:
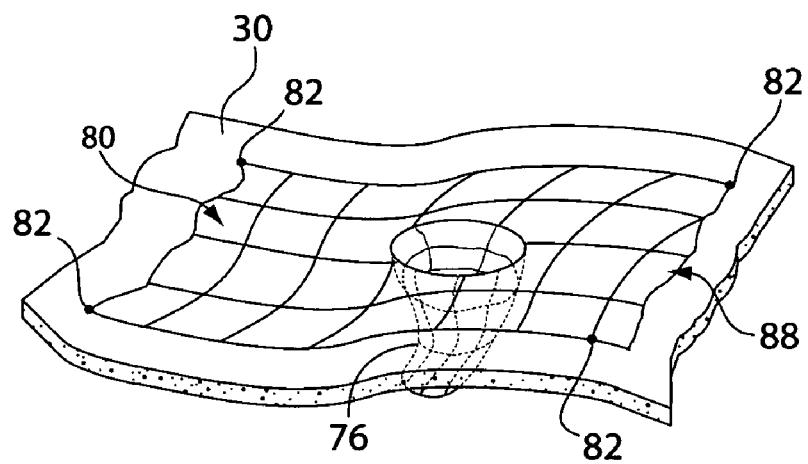
Figure 7C:
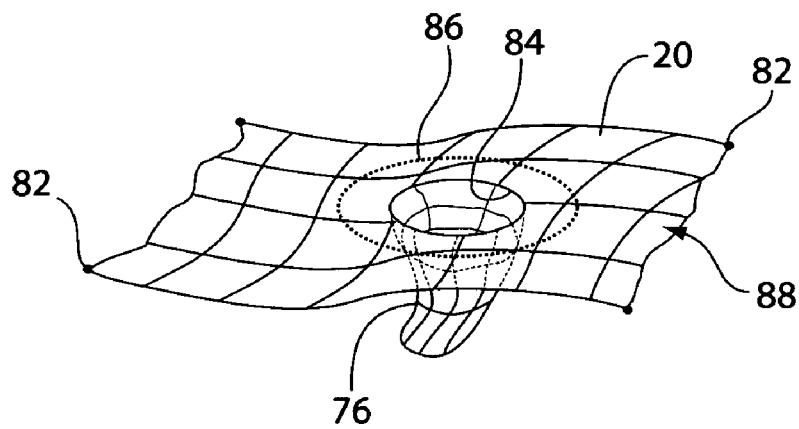

The plug 76, in a flexible embodiment thereof, may be comprised of an open sock as shown in FIG. 7a. The open sock plug 76 has a proximal end 78 thereof, is attached to the mesh 80 by the surgical adhesive/glue bonding 82 therebetween. The mesh 80 is bonded to the tissue 30 with adhesive/glue 82 as indicated in FIG. 7b. It is further contemplated that the sock-like plug 76 may be itself filled with adhesive/glue 82 to help form that plug 76. The plan view of a mesh sheet 20 is shown in FIG. 7c, with a central opening 84 for receipt of a plug therein. In this embodiment, the mesh sheet 20 has a central non-bonded flexible region 86 circularly spaced outwardly from the central opening 84. The remainder of the mesh sheet 20 is a relatively stiff bonded region 88, as indicated in FIG. 7c.

Figure 8A:
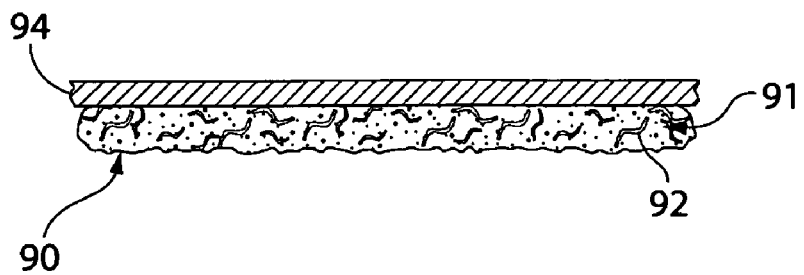
FIGS. 8a, 8b and 8c show in side elevational views of adhesive formations utilized on tissue.
Figure 8B:
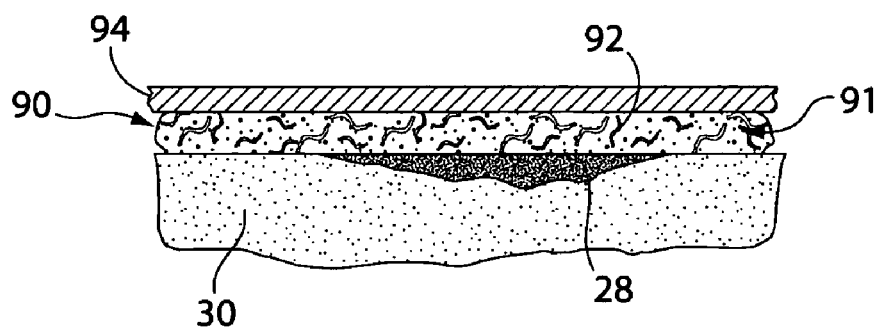
Figure 8C:
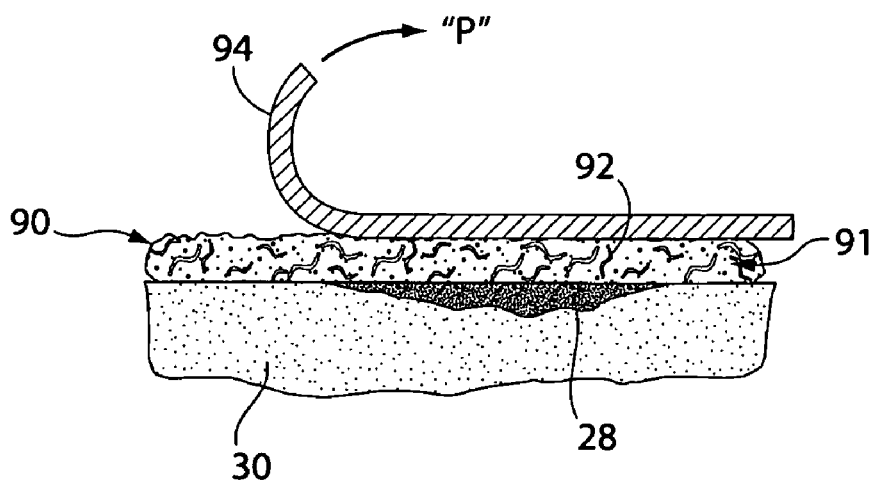

A formable mesh 90 in yet a further embodiment is shown in FIG. 8a. The formable mesh 90 is made by compounding a surgical adhesive or glue 91 with a flock 92 to give integrity to the formable mesh 90 whereupon the flock 92 stiffens that mesh 90. A protective sheet of foil 94 or the like may be applied to one side of the patch of flocked adhesive or glue 91 as indicated in FIG. 8a. The protective sheet 94 with the flocked adhesive or glue 91 on one side thereof may be rolled up and deposited onto a defect tissue site 28 on or within a patient and unrolled therein as indicated in FIG. 8b. The protective sheet 91 may be pealed from the flocked adhesive or glue once 91, as indicated by the arrow "P" in FIG. 8c, that flocked adhesive or glue thus cured onto a tissue defect site 28.

In such treatment for tissue defects, the polypropylene mesh used for the repair of tissue defects may be clear and are preferably formed in an open-weave structure. The ratio of open area to solid area is usually greater than 1. These mesh are suitable for the present invention. Even more open and flexible mesh are suitable in the present invention since the strength provided by the solid portion of the mesh can be reduced due to the binding, reinforcing, and filling character of the adhesive. For example, a mesh composed of fibers that are free to move with respect to one another would generally aneuryze when attached by sutures, but such meshes when filled with adhesive do not aneuryze, because the fibers are fixed by the adhesive. In this case, a mesh may have a porosity of 90% open area, or greater. Additionally the mesh material may be more flexible or even elastic since surface area dimensions would also be fixed by an encasing adhesive.

In further embodiments, mesh structures may be shaped to conform to certain anatomical structures, such as the sperm cord. Therefore, it may be advantageous to "color code" one or more edges of the mesh to indicate mesh orientation with respect to the structure of interest, as recited hereinabove and indicated in FIG. 4c. Additionally, coating the tissue contacting surface more thickly than the surface away from the defect minimizes the overall bulk of the device and also facilitates its rolling. In this instance, the tissue contacting side may be indicated by coloring that surface. Alternatively, in yet another preferred embodiment, the non tissue contacting side may be formed of a slowly absorbing material, since dissolution of this side during the procedure is not required to achieve fixation of the device. The dissolution of this side may take several days or weeks. Devices coated in this way may be color coded to indicate the tissue contacting side.

In a further embodiment, the non-tissue contacting side may be formed of a slowly absorbed or non-absorbable material such as methyl- or ethyl cellulose which is intended to prevent tissue adhesion. Surrounding tissue that adheres to the mesh prevents movement of the defect repair site and may cause pain. Such a tissue adhesion-prevention surface may be formed of hyaluronic acid or similar compositions, such as polyethylene glycol or the like.

Figure 6B:
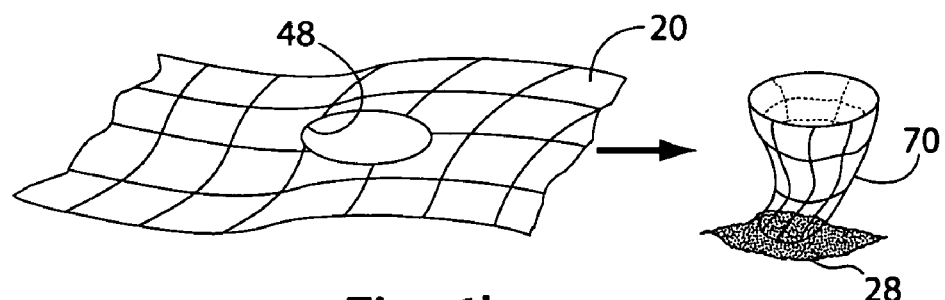

Mesh plugs may be utilized in combination with a mesh as shown in FIGS. 6a, 6b, 7a and 7b. An adhesive may be used to combine a plug 70 with a mesh 20, as shown in FIGS. 6a and 6b. In this example, the distal end of the plug would contain an adhesive that may be released by water, or alternatively, removing a protective surface and then have the mesh applied thereon. Or alternatively, the plug may contain no adhesive and the fixing mesh with adhesive is applied over the plug and surrounding tissue to fix the mesh and plug with respect to the surrounding tissue shown in FIGS. 7a and 7b. A plug/path combination may be suitably colored or marked to indicate orientation. The patch may be woven in a surface varying fashion to provide greater flexibility around the portioned intended to couple with the plug. Additionally, the adhesive may be applied to the mesh surface to provide varying amounts and thickness of adhesive to provide varying levels of mesh support with respect to the plug position. With respect to mesh and plug configuration, the mesh may contain excess adhesive in the form of an interfacing "coated and formed protuberance" of adhesive shaped to engage the plug and fix the orientation of the mesh with respect to the plug. Such a structure may fill the conical structure of the plug, and when released, it will adhere to and strengthen the plug in the implanted configuration, as may be envisioned in FIG. 7b. Thus an implant geometry can be fixed by the introduction of a substantially three-dimensional supporting-volume of adhesive. The plug may be increased in volume by the introduction of an adhesive volume that solidifies after implantation. The coating structure may be used to delinear a region of adhesive applied to the mesh surface. For instance, there are particular advantages in providing a discrete covering of adhesive over the mesh surface so that fixation points are correlated to other fixation points through the flexibility of the mesh. Exemplary patterns may be stripes, circles in a uniform pattern, circles of increasing diameter near the center, wavy lines, and the like commonly used in various other adhesive applications. Such geometries may be intended to result in traction reduction features common to sutured and stapled meshes. For instance, as the mesh become ingrown with tissue, certain sites pull against other fixed sites. A mesh with elastic contact points may be preferred in the softening of such traction. Additionally, the adhesive composition may be absorbable or weakening over time to provide for fixation points to de-adhere to the tissue surface as ingrowth replaces the need for mesh fixation. The adhesive may be comprised of a cyanoacrylate-based adhesive, a fibrin-based adhesive, a polyurethane-based adhesive, a polyisocyanate-based adhesive. The polyurethane-based adhesive may include a foaming agent added to produce an open cell geometry upon curing in situ to promote tissue ingrowth. A crosslinked albumin soldier may also be added to the prosthetic.

In general, meshes are fixed peripherally, and the distribution of fixation points across the surface of the mesh will likely lessen the incidence of extreme traction at isolated points. Delayed release of fixation through use of a coated adhesive or a slowly curing adhesive provide time for the clinician to move mesh and plug structure to positions that provide defect repair without localized stress, and further to provide optimal orientation between the two structures, or between a single mesh and anatomical structures. Accordingly, the time and cost of a hernia repair or like tissue repairs is reduced by eliminating the need for specialized, disposable fixing devices and the reduction of peri-operative and post-operative complications, since adhesions between mesh and surrounding tissue are the primary source of post-operative pain. Adhesives applied in any configuration will likely reduce adhesions by physically separating one tissue surface from the another through an adhesive coated surface.

I claim:

1. A method for repairing an internal defect in living mammalian tissue comprising covering an internal tissue defect and surrounding tissue with a prosthetic by placing said prosthetic over said defect and against said surrounding tissue; wherein the prosthetic is coated on at least one side with an adhesive before application to tissue, wherein said prosthetic is formed of a material selected from the group consisting of polytetrafluoroethylene and a fibrotic polypropylene stimulator material; and wherein said adhesive is encapsulated with a water soluble material so as to be non-adhesive until it has been placed in contact with tissue.

2. A method for repairing a defect in living mammalian tissue comprising: covering a tissue defect and surrounding tissue with a prosthetic by placing said prosthetic over said defect and against said surrounding tissue; and applying a surgical adhesive to said prosthetic on said surrounding tissue on at least one location on said prosthetic and said surrounding tissue to permit surrounding tissue and said prosthetic adhere to each other; the method further including placing at least one absorbent pad on said tissue; delivering said adhesive onto said at least one absorbent pad on said tissue; and suturing said at least one adsorbent pad to said prosthetic.

3. The method as recited in claim 1, including: applying said adhesive-containing prosthetic in situ through an endoscope.

4. The method as recited in claim 1, wherein said adhesive is selected from the group consisting of a cyanoacrylate-based adhesive, a fibrin-based adhesive, and a light-crosslinked albumin solder.

5. The method as recited in claim 1, wherein said adhesive is selected from the group consisting of a polyurethane-based adhesive and a polyisocyanate-based adhesive.

6. The method as recited in claim 5, in which said polyurethane-based adhesive includes a foaming agent added to produce an open cell geometry upon curing in situ to promote tissue ingrowth.

7. The method as recited in claim 1, wherein said adhesive is encapsulated with a coating before its application to said prosthetic.

8. The method of claim 7 wherein said coating is water soluble.

9. The method of claim 7 wherein said coating is pressure sensitive.

10. The method of claim 1, wherein the adhesive-coated prosthetic is further coated with a water soluble coating which prevents the adherence of the adhesive to tissue until the coating has dissolved.

11. The method of claim 1 wherein said water-soluble coating is applied at the time of manufacture of said prosthetic.

* * * * *